United States Patent [19]

Good et al.

[11] Patent Number: 4,873,086

[45] Date of Patent: Oct. 10, 1989

[54] HYDROGELS WITH INCREASED ORGANIC SOLVENT SOLUBLE ACTIVE AGENT LOADING CAPACITY, THEIR PREPARATION AND THE USE THEREOF

[75] Inventors: William R. Good, Suffern, N.Y.; John Mikes, Madison; Joseph Sikora, Wanaque, both of N.J.

[73] Assignee: Ciba-Geigy Corporation, Ardsley, N.Y.

[21] Appl. No.: 229,189

[22] Filed: Aug. 8, 1988

Related U.S. Application Data

[63] Continuation of Ser. No. 835,414, Mar. 3, 1986, abandoned.

[51] Int. Cl.$^4$ ..................... A61K 31/78; A61K 31/74
[52] U.S. Cl. .................... 424/409; 514/944; 514/950; 528/75; 528/904; 424/78; 424/81; 424/486; 424/487
[58] Field of Search ............... 424/81, 78, 409, 486, 424/487; 514/944, 950; 528/75, 904

[56] References Cited

U.S. PATENT DOCUMENTS

| | | | |
|---|---|---|---|
| 4,127,127 | 11/1978 | Wong et al. | 128/260 |
| 4,177,056 | 12/1979 | Mueller et al. | 71/93 |
| 4,304,591 | 12/1981 | Mueller et al. | 71/93 |
| 4,548,990 | 10/1985 | Mueller et al. | 525/123 |

*Primary Examiner*—John S. Maples
*Attorney, Agent, or Firm*—Irving M. Fishman

[57] ABSTRACT

An organic solvent soluble active agent containing water-insoluble hydrophilic hydrogel comprising a copolymer of (A) a water-soluble monoolefinic monomer or a mixture thereof optimally containing up to 50% thereof of one or more water-insoluble mono-olefinic monomers and (B) a terminally diolefinic hydrophobic macromer containing polypropylene oxide or polytetramethylene oxide units prepared in the presence of an effective macromer expanding amount of a macromer soluble compound of the formula $$R'(R''-O)_nR'''$$

where R', R", R''' and n are as defined in the claims, hydrogels useful in the loading of such active agents, their preparation, and use are disclosed.

15 Claims, No Drawings

HYDROGELS WITH INCREASED ORGANIC SOLVENT SOLUBLE ACTIVE AGENT LOADING CAPACITY, THEIR PREPARATION AND THE USE THEREOF

This is a continuation of application Ser. No. 835,414 filed on Mar. 3, 1986, now abandoned.

BACKGROUND OF THE INVENTION

This invention relates to improved water-soluble hydrogels which are in the form of macromer-crosslinked polymers of one or more water-soluble monoolefinic monomers, optionally containing a minor amount of one or more water-insoluble monoolefinic monomers having superior active agent loading capacity. The macromer component is a terminally diolefinic hydrophobic macromer containing a polypropylene oxide or polytetramethylene oxide diradical in the macromer chain. These hydrogels can be loaded with active agents, especially biologically active agents, including pharmaceuticals, insecticides, herbicides, and the like, for the controlled, sustained release thereof by diffusion upon contact with an aqueous environment.

Hydrophilic hydrogels in the form of macromer-crosslinked polymers containing monomer and macromer components are known, for example, in U.S. Pat. No. 4,177,056, the disclosure of which is incorporated herein by reference in toto in regard to eligible components, including active agents, monomers and macromers; polymer preparation, including process parameters and modes of preparation; active agent loading techniques, and the use thereof; and preferred embodiments in respect to such components, preparation, loading techniques, and use.

It has been surprisingly and unexpectedly discovered, in accordance with the instant invention, that the nature of the macromer-crosslinked polymers can be substantially and irrevocably modified so as to increase the organic solvent swelling characteristics of the polymers. As a result, the amount of organic solvent soluble active agent capable of being loaded into such polymers can be greatly increased.

This modification of the macromer-crosslinked polymers is obtained by conducting the polymerization in the presence of certain macromer compatible compounds. Such compounds act as macromer expanders by increasing the organic solvent soluble active agent loadability. But, by virtue of their solubility in the macromer component, both prior to and during polymerization, the macromer expanding compounds do not occasion the formation of copolymers having a macroporous structure. Macroporous copolymers are generally characterized in having pores ranging from about 100–5000 Angstroms. Various cross-linked macroporous polymers are disclosed, for example, in U.S. Pat. No. 3,509,078. In contrast to macroporous copolymers, the instant macromer expanded copolymers are substantially free from macroporosity. As a result, the instant glossy, i.e., optically clear to hazy, copolymers release the active agent by controlled diffusion upon contact with an aqueous environment, in contrast to convectional paths and the like, occasioned by macroporous networks.

It is an object of the present invention to provide novel macromer expanded hydrogel polymers having substantially increased organic solvent soluble active agent loadability and their preparation and use.

It is a further object of the present invention to provide active agent loaded controlled, sustained release compositions of such polymers and their preparation and use.

These and other objects of the present invention are apparent from the following description.

DETAILED DESCRIPTION OF THE INVENTION

One embodiment of the present invention relates to a process for the production of a controlled, sustained release composition comprising:

(a) an organic-solvent soluble active agent in an amount sufficient for the total desire dosage during the release period and distributed within.

(b) a water-insoluble macromer expanded hydrogel comprising the crosslinked copolymerization product of (A) about 30 to about 90% by weight of said hydrogel of (a') a water-soluble monoolefinic monomer, or mixture of said monomers, or (b') a water-soluble monoolefinic monomer, or mixture of said monomers with 1 to 50% by weight of total monomers of a waterinsoluble monoolefinic monomer, or mixture of said water-insoluble monomers, with (B) about 70 to about 10% by weight of said hydrogel of a terminal diolefinic hydrophobic macromer having a molecular weight from about 400 to about 8000, said macromer having the formula

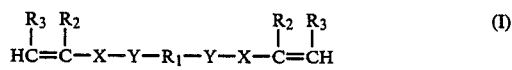

wherein $R_1$ is a polycondensate chain having a molecular weight from about 200 to about 8000, which is the residue of a poly(propylene oxide) or poly(tetramethylene oxide) glycol having other linkages; $R_2$ is hydrogen, methyl or $-CH_2COOR_4$ wherein $R_4$ is hydrogen or an alkyl group with up to ten carbon atoms; $R_3$ is hydrogen or $-COOR_4$, with the proviso that at least one of $R_2$ and $R_3$ is hydrogen; X is oxa, $-COO-$, or $-CONR_5-$ wherein $R_5$ is hydrogen or alkyl of up to 5 carbon atoms and Y is a direct bond or the radical $-R_6-Z_1-CO-NH-R_7-NH-CO-Z_2-$, wherein $R_6$ is linked to X and represents branched or linear alkylene of up to 7 carbon atoms, $Z_1$ and $Z_2$ are oxa or $NR_5$, and $R_7$ is the diradical of an aliphatic including cycloaliphatic or aromatic diisocyanate, with the proviso that in X is oxa, Y is different from a direct bond, and $R_2$ and $R_3$ are hydrogen; comprising the steps of copolymerizing said monomer (A) and said macromer (B) in the presence of a free radical initiator at a reaction temperature between about 20° to about 150° C., in the presence or absence of a substantially inert diluent, and in the presence of an effective macromer (B) expanding amount of a macromer (B) soluble compound of the formula

wherein R
wherein R' is HO—, alkoxy of up to eight carbon atoms or alkanoyloalkanoyloxy of up to eight carbon atoms; R" is straight or branched chain alkchain alkylene of two to six carbon atoms; R'" is hydrogen, alkyl of up to eighteen carbon atoms or alkanoyl of up to eighteen carbon atoms; and n is an integer from 1 to about 100, with the proviso that if n is 1 or R" is ethylene, R'" is alkyl of two to eighteen carbon atoms or alkanoyl of three to eighteen carbon atoms, or a mixture thereof; to form said hydrogel, and loading said active agent (a) into said hydrogel.

An alternate embodiment of the invention relates to the water-insoluble macromer expanded hydrogel itself, useful as an intermediate in preparation of the active agent loaded composition, and prepared in accordance with the preceeding paragraph, excluding the loading of active agent (a) into said hydrogel.

A further alternate embodiment relates to the active agent loaded composition produced, and its use in a method of releasing the active agent; such as the oral administration of an effective amount of a pharmaceutically effective active agent to a host, e.g. a patient, in need of such active agent.

By the expression, "an effective macromer (B) expanding amount", in relation to the compound of Formula II, or mixture thereof, is meant an amount sufficient to substantially increase the organic solvent swelling characteristics, and consequently the organic solvent soluble active agent loadability of the resultant hydrogel, in comparison with an otherwise identical hydrogel but prepared in the absence of such compound of Formula II, or mixture thereof. The amount of compound of Formula II or mixture thereof incorporated in the monomer/macromer mixture during, or preferably prior to, the polymerization step can vary widely, but is usually between about 5 to about 70 weight percent, preferably between about 10 and about 60 weight percent, of the total weight of monomer (A) and macromer (B). The amount of increased organic solvent swellability, as measured using one or more conventional organic swelling solvents, is generally proportional to the amount of compound of Formula II employed. Suitable organic swelling solvents for determining increased swellability, and for loading the macromer expanded hydrogels by dissolving the active agent into said solvent and inbibing the active agent solution into the hydrogel, include lower alkanols, such as methanol or ethanol; lower alkanones, such as acetone or methyl ethyl ketone; di-lower alkyl ethers, such as ethyl ether; lower alkanoic acids, such as propionic acid; lower alkyl esters of lower alkanoic acids, such as ethyl acetate; lower alkylene oxides, such as tetrahydrofuran; and lower partially halogenated alkanes, such as methylene chloride or chloroform. Especially convenient are relatively volatile organic polar solvents, such as methanol, ethanol, methylene chloride or mixtures thereof. Water may be present in such organic solvents, and, in certain cases aqueous organic solvent systems, such as an aqueous ethanol solvent, have been found to be highly advantageous as a suitable organic solvent swelling medium, e.g. for loading active agents soluble therein.

The amount of increased organic solvent swellability of the instant macromer expanded hydrogels in comparison to their nonmacromer expanded hydrogen counterparts is preferably between about 5 to about 120%, most preferably between about 20 to about 90%, by weight, using ethanol as a swelling solvent. Generally the macromer expander of Formula II is removed prior to such comparative swelling.

While the organic solvent swellability, e.g. as measured using ethanol, can be increased dramatically using the instant macromer expanded hydrogels, thereby providing for an increased loadability of organic solvent soluble active agent, in many cases the aqueous swellability, using e.g. water as a swelling agent, is increased only slightly or not at all. As a result, an additional advantage is realized in such cases, since the increase in loading capability of active agent can be achieved without significant increase in the rate of diffusion of active agent into the desired environment upon contact of the loaded composition with an aqueous medium.

Suitable compounds of Formula II, as indicated above, must be soluble in the macromer component both prior to and during polymerization, such that the polymerization proceeds in essentially a single phase. Accordingly, those compounds of Formula II, wherein n is 1, R' is HO— and R''' is hydrogen, such as ethylene glycol or propylene glycol, or where R' is HO—, R'' is hydrogen and R'' is ethylene, such as polyethylene oxide, are unsuitable due to their insufficient solubility, or compatibility, in the macromer component. However, derivatives of such compounds, where R''' is sufficiently hydrophobic, such as ethylene glycol monobutyl ether or ethylene glycol monobutyl ether acetate, and the like, possess sufficient solubility or miscibility in the macromer component prior to and during polymerization so as to result in the desired macromer expanded polymer.

In a preferred embodiment of the compounds of Formula II, R' is hydroxy or alkanoyloxy of up to three carbon atoms, R'' is alkylene four carbon atoms, n is 1 and R''' is alkyl of three to six carbon atoms. Examples of such preferred compounds include, for example, ethylene glycol monobutyl ether, ethylene glycol monobutyl ether acetate, and the like.

An alternate preferred embodiment of the compounds of Formula II includes compounds of the formula

$$HO(-R''-O)_nH \qquad (III)$$

where n has an average value between about 9 and about 60 and R'' is alkylene of three or four carbon atoms. Highly preferred are compounds of Formula III, wherein n has an average value between about 25 and 80 and R''' is isopropylene and also those compounds of Formula III, wherein n has an average value between about 8 and 40 and R'' is tetramethylene. Suitable such compounds include polypropylene glycols having an average molecular weight of about 2000 or about 4000, and polytetramethylene glycols having an average molecular weight of about 650, 1000, and 2000.

Preferred monomers (A) include those water soluble monomers which are acrylic or methacrylic acid or water-soluble esters, amides or imines thereof, especially acrylic or methacrylic acid, or hydroxyalkyl or dialkylaminoalkyl esters thereof in which alkyl in each case has two to four carbon atoms. Suitable water-soluble monomers for use in accordance with the instant invention are recited in U.S. Pat. No. 4,177,056 and include, f example, acrylic acid, methacrylic acid, 2-hydroxyethyl or 2- or 3-hydroxypropyl acrylate or methacrylate, N-vinylpyrrolidone or tertiary methyl aminomethyl acrylamide, or mixtures thereof. Most preferred monomers are 2-hydroxyethyl methacrylate and N-vinylpyrrolidone.

Preferred water-insoluble olefinic monomers include alkyl acrylates or methacrylates, where alkyl has one to eighteen carbon atoms, e.g. methyl and ethyl methacrylate or acrylate; vinyl esters of alkanoic acids of up to five carbon atoms, e.g. vinyl acetate, acrylonitrile, styrene, and vinyl alkyl ethers where alkyl has up to five carbon atoms, e.g. ethyl vinyl ether.

Preferred macromer (B) components include those of Formula I wherein the macromer is a reaction product of (1) a polypropylene or polytetramethylene oxide glycol with a molecular weight of about 600 to about 4000, which is encapped for example, with isophorone diisocyanate and (ii) two moles, per mole of said glycol, of a hydroxyalkyl acrylate or methacrylate of 2 to 4 carbon atoms.

The polymerization can be carried out in the presence of a conventional free radical initiator, including peroxides, such as benzoyl peroxide or t-butyl perocloate; percarbonates, such as diisopropyl percarbonate; azonitriles, such as azoisobutyronitrile; persulfates, such as sodium persulfate; or other free radical generators, such as gamma rays, electron beams, and ultraviolet radiation.

The reaction temperature may vary widely and is limited only by the stability of the ingredients. Suitable reaction temperatures range from about 20° C. to about 150° C., preferably between about 50° C. to about 100° C. The hydrogel containing macromer may be prepared in the presence or absence of an inert diluent, in a closed mold, e.g. to form flat sheet or cylinder. Alternatively, the hydrogel may be prepared in the form of small spheres or beads, comprising the high speed stirring of the macromer, monomers, expander, catalyst and optionally active agent in a viscous medium which is not a solvent for any part of the hydrogel composition at a temperature between about 50° C. and 100° C. Examples of suitable bead polymerization media are silicone oils, polyfluorinated oils, mineral spirit and saturated aqueous salt solutions.

Incorporation of the active agent into the hydrogel article may be accomplished either by dissolution or dispersion in the macromer solution prior to or during the copolymerization of macromer and monomer, or by diffusion into the macromer expanded hydrogel from an organic solvent medium containing the active agent subsequent to the copolymerization. In this latter embodiment, the macromer expanded hydrogel may be washed with a solvent to remove the compound of Formula II, prior to the incorporation, or loading, of the hydrogel with active agent. Suitable solvents for use in removing the compound of Formula II from the macromer hydrogel include those organic swelling solvents recited above. After removal of the compound of Formula II from the macromer hydrogel, the hydrogel may be dried, e.g. by solvent evaporation. Likewise, after the active agent is loaded into the hydrogel from a suitable solvent medium, the active agent loaded hydrogel can be dried by solvent evaporation. Upon contact with an aqueous environment, the active agent will be released in a controlled sustained manner.

Suitable active agents are pharmaceuticals, herbicides, insecticides, flavoring agents, nutrients, fungicides, bacteriocides, and the like, which are at least partially soluble in the chosen organic swelling solvent. Suitable active agents, include without limitation, those listed in U.S. Pat. No. 3,732,865 (Columns 10 and 11), U.S. Pat. No. 4,177,056 (Columns 10 and 11) and U.S. Pat. No. 3,660,563 (Columns 3 to 7). Preferred active agents include pharmaceuticals, herbicides, and insecticides. In the field of pharmaceuticals, the loaded hydrogels can be activated by ingestion into the gastrointestinal tract, wherein the active pharmaceutical is released upon contact with aqueous gastrointestinal fluid in a controlled sustained manner. For agricultural purposes, the active agent loaded hydrogel can be incorporated into the soil to release the active herbicide, insecticide, nutrient, or the like, in the presence of moist soil conditions.

The amount of active agent loaded into the macromer hydrogel will vary widely depending on the desired effect, the active agent employed, and the time span for which it takes the active agent to be released. For pharmaceutical applications, for example, the upper and lower limits of pharmaceutical agent incorporated will depend on the activity of the pharmaceutical, e.g. drug, and the span of its release in the carrier. Preferred drugs to be incorporated are those designed for long-term treatment so that multiple daily doses can be avoided, for example, anabolics; analgesics; anti-inflammatories, e.g. dichlofenac sodium, asperin, phenylbutozone or methadone; antibiotics, e.g. rifampin; antidepressants, e.g. imipramine or maprotiline; anticonvulsives, e.g. carbamazepine; antihypertensives, e.g. hydralazine antiparasitics, e.g. nifurtimox; bronchiodilators, e.g. fenoterol; coronary dilators, e.g. fenalcomine; corticoids, e.g. dexamethasone; diuretics, e.g. hydrochlorothiazide; hypnotics, e.g. glutethimide; neuroleptics, e.g. reserpine; tranquilizers, e.g. diazepam; or vasodilators, e.g. isoproterenol. Preferred pharmaceuticals include diclofenac sodium and carbmazepine.

The loaded macromer expanded hydrogels are advantageously stored in the dry state, e.g. by removal of the loading organic solvent from the loaded hydrogels by evaporation.

The following non-limiting examples are set forth as illustrative of the instant invention. All parts are by weight unless otherwise specified.

EXAMPLE 1

Bulk Polymerization of a Hydrogel

A glass plate was framed with 0.5 mm thick teflon rims and covered, with mylar foil, leaving a small opening at a corner of mold. Nitrogen was passed through for 10 minutes. A monomer/macromer was charged in through the opening and vacuum-treated to make it bubble-free.

The monomer/macromer was prepared by dissolving 600 gm (0.24 moles) of a poly-(tetramethylene oxide) glycol with an average molecular weight of 2000 endcapped with isophorone diisocyanate in 900 gm (7 moles) of 2-hydroxyethyl methacrylate (HEMA) and allowing said mixture to react for 72 hours at 30° C. At the end of this period, the disappearance of the terminal isocyanate group was verified by noting the absence of the characteristic infrared spectral band at 2270 cm$^{-1}$ associated with the—NCO group. The composition of the monomer/macromer made of 900 gm (60%) HEMA (hydroxyethyl methacrylate) and 600 gm (40%) isocyanate encapped polyether is marked as a "6040" composition. Similar nomenclature is used throughout the examples for the composition of the amphiphilic copolymers. 0.02% of azo-bis-isobutyronitrile initiator was added to the monomer/macromer charged into the flat cavity between glass and mylar sheet bubble-free. After closing the corner-opening of the mold the assembly was placed in a 70° C. oven for 4 hours. Subsequently, the polymer film was removed from the mold; extracted free from residual monomers, oligomers, and other impurities and kept wet for further testing.

EXAMPLE 2

Same procedure was followed as in Example 1, with the exception that 0.24 moles of poly-(propylene oxide) glycol (molecular weight of 2000) was used instead of the tetramethylene compound in the synthesis of the macromer.

EXAMPLE 3

Same procedure was followed as in Example 1, with the exception of dissolving 25 gm of P-PRG-2000, i.e. poly-(propylene oxide) glycol (molecular weight 2000), in 100 gm of the monomer/macromer mixture before charging it into the mold. The polymer film was carefully extracted with alcohol until all expander was removed.

EXAMPLE 4

Same procedure was performed as described in Example 2 using the variance as described in Example 3.

EXAMPLE 5

The procedure as described in Example 1 was followed with the variance of adding 40 gm of EB-AC, i.e. ethylene glycol monobutyl acetate as macromer expander, to 100 gm of the monomer/macromer before charging it into the mold. The polymer film was boiled in water under reduced pressure to remove the expander by an azeotropic distillation.

EXAMPLE 6

The process as described in Example 2 was followed with the variance described in Example 5.

TABLE 1-6

| Polymer of | Expander | % | DS-0 (1) | DS-100 (2) |
|---|---|---|---|---|
| Example #1 | — | — | 20.7% | 56.8% |
| Example #2 | — | — | 22.1% | 83.0% |
| Example #3 | P-PRGL-2000 (*) | 25 | 19.1% | 66.5% |
| Example #4 | P-PRGL-2000 (*) | 25 | 21.9% | 101.0% |
| Example #5 | EB-AC | 40 | 17.6% | 79.8% |
| Example #6 | EB-AC | 40 | 22.3% | 121.0% |

(*) Polyglycol-2000, Dow.
(1) and (2) are the degree of swelling (%).
(1) 100% water swelling
(2) 100% ethanol swelling. The percent swelling is calculated: (weight of swollen polymer - weight of dry polymer) × 100 ÷ the weight of the dry polymer.

EXAMPLE 7

Suspension Polymer Preparation—6040

A smooth wall, 1000 ml resin flask was equipped with a reflux condenser, nitrogen inlet tube, thermometer—attached to a thermoregulator, a paddle type stirrer driven by a variable motor. A slow nitrogen purge was maintained through the system at all times.

Charged into the flask were 360 gm of a 20% by weight aqueous sodium chloride solution containing 41 gm (0.2 moles) of magnesium chloride hexahydrate. The solution was heated to 80° C. and with a rapid stirring 123 ml (0.123 moles) of 1.N NaOH was added dropwise. When all the sodium hydroxide was added, the stirring speed was adjusted to 180 rpm and 180 gm of monomer/macromer mix—with the initiator in it as described in Example 1—was added. After three hours the temperature was raised to 100° C. for one more hour. The reaction was cooled to dissolve the Mg(OH)$_2$ suspension agent. The isolated beads were washed and extracted in alcohol to remove any residual monomer or oligomer and other impurities. After eight hours, vacuum drying at 60° C. 173 gm (95% yield) bead polymer were obtained with an average diameter of 0.9 mm.

EXAMPLE 8

Suspension Polymer Preparation—6535

The procedure of Example 7 was followed with only one variance: The composition of the monomer/macromer as described in Example 1 was changed by dissolving the 600 gm isocyanate-endcapped poly-(butylene oxide) glycol in 1114 gm HEMA (weight ratio 35 to 65). The rest of the procedure is identical to the one described in the preceding example. Yield was 173.5 gm (96.4%), with an average bead diameter of 0.85 mm.

EXAMPLES 9-10

The process of Example 7 was applied with the exception of using mixtures of monomer/macromer and butylene glycol mono-ethyl ether acetate (Ektasolve EBAC - Eastman Kodak) as expander/additive. In preparation of the #9 mixture, the 180 gm monomer/macromer phase consisted of 36 gm EBAC and 144 gm monomer/macromer; in #10 the mix contained 112.5 gm monomer/macromer and 67.5 gm EBAC. The post-heat of the process was carried out at 700 mmHg pressure with a descending condenser attached to the flask and continued with constant replacement of the distillate volume by deionized water until the condensate was free of the EBAC odor—about 2 hours. Yield: 136 gm—94.4% for Example 9 product and 105.3 gm—93.6% for the polymer of Example 10. Average bead diameters: 0.72 and 0.61 mm, respectively.

EXAMPLES 11-12

Using the procedure described in Example 8, the process of copolymerization was performed as shown in the preceding Examples Nos. 9 and 10. The composition of the monomer/macromer Example 11: 144 gm monomer/macromer and 36 gm Ektasolve EB (ethylene glycol monobutyl ether, Eastman Kodak) and in Example 12 to 120 gm monomer/macromer 60 gm of the EB additive. The yields were 136.8 gm—95% with an average bead diameter of 0.72 mm and 113.4 gm—94.5% (average diameter 0.64 mm), respectively.

TABLES 7-12

The products of Example Nos. 7 to 12 were tested for swelling % in water (DS-0) and ethanol (DS-100) and some were tested for the loading capacity and release rate of diclofenac sodium as an active ingredient.

| Example | Comp. | Additive | % | DS-O | DS-100 | Load-% | T-50(*) | T-90(*) |
|---|---|---|---|---|---|---|---|---|
| #7 | 6040 | — | — | 27% | 60% | 28.2 | 6.95 | 31 |
| 8 | 6535 | — | — | 32% | 64% | 30.0 | 2.33 | 21.3 |
| 9 | 6040 | EB-AC | 25 | 32% | 87% | N.A. | | |
| 10 | 6040 | EB-AC | 60 | 41% | 122% | 46 | 1.41 | 21 |
| 11 | 6535 | EB | 25 | 38% | 95% | N.A. | | |

-continued

| Example | Comp. | Additive | % | DS-O | DS-100 | Load-% | T-50(*) | T-90(*) |
|---------|-------|----------|-----|------|--------|--------|---------|---------|
| 12 | 6535 | EB | 50 | 43% | 115% | N.A. | | |

(*)Hours elapsed while releasing 50%/90% active ingredient

EXAMPLE 13

Suspension Polymer Preparation -5050

Using the procedure of Example 7 with 180 gm monomer/macromer mix of 600 gm HEMA and 600 gm of the isocyanate encapped poly(butylene oxide) glycol, molecular weight 2000 (polymeg 2000 of Quaker Oats), the yield was 176.5 gm (98.9% bead copolymer of an average diameter of 1.1 mm.

EXAMPLES 14-18

Expanded copolymer hydrogels using the procedure of Example 13 with poly-propylene oxide) glycol, molecular weight 2000 (polyglycol 2000 of Dow) as the expanding additive, the compositions of the monomer phases were:
14 —171.4 gm monomer/macromer+8.6 gm PG 2000
15 —163.6 gm monomer/macromer+17.8 gm PG 2000
16 —156.5 gm monomer/macromer+23.5 gm PG 2000
17 —150.0 gm monomer/macromer+30.0 gm PG 2000
18 —144.0 gm monomer/macromer+36.0 gm PG 2000

Yields and average particle size values were measured after an alcoholic extraction of the additive from the beads. The results are #14: 167.6 gm /98%/ 1.1 mm; #15: 157.3 gm /97.2%/ 1.0 mm; #16: 150.0 gm /98%/ 1.0 mm; #17: 142.5 gm /99%/ 0.98 mm; #18: 131.0 gm /97%/ 0.99 mm. Swelling tests were performed and diclofenac loadability % was assayed. The results are as follows:

TABLES 13-18

| Example | Comp. | Additive | % | DS-0 | DS-100 | Load-% |
|---------|-------|----------|-----|------|--------|--------|
| #13 | 5050 | — | — | 21% | 54% | 26 |
| #14 | 5050 | PG2000 | 5 | 23% | 56% | 27 |
| #15 | 5050 | PG2000 | 10 | 23% | 57% | 29 |
| #16 | 5050 | PG2000 | 15 | 20% | 62% | 29 |
| #17 | 5050 | PG2000 | 20 | 22% | 67% | 32 |
| #18 | 5050 | PG2000 | 25 | 20% | 69% | 32 |

EXAMPLES 19-25

A similar series has been prepared to the Examples 13-18, using the procedure of Example 8. With expander additive amounts of poly-(butylene oxide) glycol, molecular weight 1000 (polymeg 1000 of Quaker Oats), the compositions of the monomer phases in runs 19-23 were identical to the amounts given in Examples 14-18, respectively. Example 24 contained 138.5 gm monomer/macromer plus 41.5 gm PM1000 and Example 25 was polymerized from a monomer phase containing 133.33 gm monomer/macromer with 46.66 gm PM1000. Yields and average particle sizes in the Examples 19-25 were:
19—170 gm/99%, 0.84 mmφ
20—158.9 gm/98.1%, 0.86 mmφ
21—149.3 gm/97.6%, 0.84 mmφ
22—146.2 gm/97.5%, 0.83 mmφ
23—147 gm/98%, 0.85 mmφ
24—134.3 gm/97%, 0.83 mmφ
25—129.3 gm/97%, 0.85 mmφ

The test results are:

TABLE 19-25

(Comparative data of Example 8, the unexpanded 6535 composition copolymer hydrogel, are shown)

| Example | Comp. | Additive | % | Swelling % DS-0 | Swelling % DS-100 | Maximum Loading | Release Hrs T-50 | Release Hrs T-90 |
|---------|-------|----------|-----|------|--------|-----------------|------|------|
| #8 | 6535 | — | — | 32 | 64 | 30% | 2.33 | 21.3 |
| #19 | 6535 | PM-1000 | 5 | 32 | 74 | 30% | 2.7 | 18 |
| #20 | 6535 | PM-1000 | 10 | 29 | 75 | 33.6% | 3.2 | 21 |
| #21 | 6535 | PM-1000 | 15 | 30 | 80 | 35.7% | 3.0 | >21 |
| #22 | 6535 | PM-1000 | 20 | 29 | 82.5 | 36.2% | 3.1 | >21 |
| #23 | 6535 | PM-1000 | 25 | 29 | 85 | 38.4% | 2.7 | >21 |
| #24 | 6535 | PM-1000 | 30 | 28.5 | 88 | 38.0% | 2.2 | 20 |
| #25 | 6535 | PM-1000 | 35 | 30 | 97 | 39.8% | 1.7 | 20 |

EXAMPLE 26

Preparation of Copolymer Hydrogel 9010

Using the method of copolymerization described in Example 7, the composition of the monomer/macromer was adjusted to 1800 gm HEMA dissolving 200 gm of isocyanate encapped polymeg 2000 intermediate. The resulting monomer/macromer is of lower viscosity, accordingly the polymerization was done at 150 rpm stirring rate resulting in a bead product of 0.55 mmφ average particle size.

EXAMPLE 27

Using the process of Example 26 in this expanded copolymerization, the monomer phase was composed of 144 gm monomer/macromer and 36 gm of polymeg 2000. The average bead size of the dry product after alcoholic extraction was 0.98 mmφ.

EXAMPLE 28

The procedure of Example 27 was carried out using polymeg 1000 instead of the polymeg 2000 as the expander-additive. The average bead diameter was 0.86 mm.

EXAMPLE 29

The procedure of Example 27 was carried out using polymeg 650 as the expander instead of the polymeg 2000 used above. The average polymer bead size was 0.72 mm in diameter. Below are shown the swelling characteristics of 9010 copolymer hydrogels with diverse molecular weight expander additives (+25% each). An intermediate ethanol/water medium (55% ethanol) was added to the tests (DS-55).

TABLE 26-29

| Example 26 | DS-0: | 54% | DS-55: | 152% | DS-100: | 80% |
| Example 27 | DS-0: | 55% | DS-55: | 226% | DS-100: | 120% |
| Example 28 | DS-0: | 56% | DS-55: | 195% | DS-100: | 100% |
| Example 29 | DS-0: | 56% | DS-55: | 175% | DS-100: | 89% |

EXAMPLE 30

This example shows the preparation of controlled swelling hydrogels by the use of both hydrophobic co-monomers in the amphiphilic composition and expander additives. Four copolymers were prepared according to the procedure shown in Example 8.

A. The comparative, unchanged Example 8 hydrogel;

B. The unexpanded copolymer containing a hydrophobic comonomer in the composition: 156.5 gm monomer/macromer plus 23.5 gm of butyl mathacrylate (monomer/macromer "B");

C. The expanded "A" copolymer as in Example 12;

D. The expanded "B" copolymer by mixing 51.4 gm ethylene glycol monobutyl ether acetate expander to 128.6 gm of the monomer/macromer used in the "B" run. The products were tested for their swelling behavior:

A: DS-0=32% DS-100=53%
B: DS-0=29% DS-100=100% (DS-75=137%)
C: DS-0=45% DS-100=114%
D: DS-0=29% DS-100=148% (DS-75=202%)

EXAMPLE 31

A variant of Sample "D" in the preceding example was prepared starting with a 6050 monomer/macromer as described in Example 7. 107.2 grams of it was mixed with 21.4 gm butyl methacrylate and 51.4 gm Ektasolve EBAC. Polymerization was performed as shown in Examples 9-10.

Comparison of swelling data of the Example 31 hydrogel, the Example 10 polymer (a 6040 composition with 60% ethylene glycol monobutyl ether acetate), and those of Example 7, without modifying additives, shows aqueous swelling (DS-0): #7=27%, #10=41%, #31=23%; and ethanol swelling (DS-100): #7=60%, #10=122%, #31=139%.

EXAMPLE 32

300 g isophorone diisocyanate/poly-(tetramethylene oxide) condensate macromer of Example 1 was dissolved in 1200 g hydroxyethyl methacrylate, containing 1.2 g t-butyl peroctoate. After degassing for one hour at 0.5 mmHg pressure, 750 g polymeg 2000 were dissolved in the mix. The composition was distributed by a turbine mixer in a 10 lit reactor in the 85° C. ready aqueous phase of 3,484 g DI water/868.4 g NaCL/397.2 g of a MgCl$_2$·6H$_2$O1:1 aqueous solution, which was heated under N$_2$ purging to 70° C. and 934.5 ml 1.N NaOH stirred in at 125 rpm with further heating.

Stirrer was adjusted to 80 rpm and the system was kept at 95°-100° C. for two hours. After thorough washing, the bead polymer was filtered and extracted with hot alcohol until all expanding polymeg 2000 was removed. Vacuum drying at 80°-90° C. and screening completed the preparation.

EXAMPLE 33

The procedure of Example 32 was carried out with the addition of 50% poly-(propylene oxide) glycol expander in lieu of polymeg 2000.

EXAMPLE 34

Hydrogel beads of both Examples 32 and 33 were loaded with carbamazepine in identical runs: 58.3 gm of 80:20 methylene chloride/methanol was stirred and 16.7 gm carbamazepine was dissolved at room temperature. 20 g hydrogel beads of —40+45 mesh bead size were added and stirred for 48 hours. After complete absorption, the material was dried at room temperature and 3 mmHg vacuum. The loaded beads in gelatin capsule #0 contained 200 mg active ingredient.

Release Rates:
Example 32 T-50=0.4 hr T-90=1.9 hr
Example 33 T-50=0.5 hr T-90=2.25 hr
as per USP Apparatus II (100 rpm). Comparative release rate test using 200 mg carbamazepine tablets gave T-50 and T-90 values of 0.5 and 3 hours, respectively.

EXAMPLE 35

A hydrogel polymer of Example 7, in bead form, is soaked in a 75% by weight solution of diclofenac sodium dissolved in a medium of 88% methanol and 12% distilled water. The mixture is rotated at 30-60 revolutions per minute at 39°-41° C. for about 24 hours whereby the solution is inbibed into the beads and equilibrium is achieved. The solvent is then removed by freeze drying at <0.2 mm Hg pressure for 3 hours, with additional vacuum drying for 22 hours at room temperature, whereby the loaded hydrogen is achieved.

In the same manner, the hydrogels of Example 8, 10, and 19-25 are also loaded with diclofemac sodium.

EXAMPLE 36

200g of the expanded hydrogel beads of Example 19 are added to a solution of 132.9g of diclofenac sodium in a mixture of 139.8g methanol and 200g distilled water. The temperature is maintained at about 40° C. and the mixture rotated for 24 hours. The solvent is removed by freeze drying at 0.2 mm Hg over a period of about 3 hours with additional drying at room temperature for about 22 hours to result in a 98% yield of 30% diclofenac sodium loaded hydrogel product.

We claim:

1. A process for the preparation of a controlled, sustained release composition comprising:
   (a) an organic-solvent soluble active agent in an amount sufficient for the total desired dosage during the release period and distributed within
   (b) a water-insoluble macromer expanded hydrogel comprising the crosslinked copolymerization product of
   (A) about 30 to about 90% by weight of said hydrogel of (a') a water-soluble monoolefinic monomer, or mixture of said monomers, of (b') a water-soluble monoolefinic monomer, or mixture of said monomers with 1 to 50% by weight of total monomers of a water-insoluble monoolefinic monomer, or mixture of said water-insoluble monomers, with
   (B) about 70 to about 10% by weight of said hydrogel of a terminal diolefinic hydrophobic macromer having a molecular weight from about 400 to about 8000, said macromer having the formula

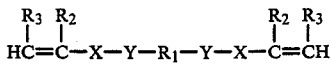

wherein $R_1$ is a polycondensate chain having a molecular weight from about 200 and about 8000, which is the residue of a poly (propylene oxide) or poly(tetramethylene oxide) glycol having ether linkages; $R_2$ is hydrogen, methyl or —$CH_2COOR_4$ wherein $R_4$ is hydrogen or an alkyl group with up to 10 carbon atoms; $R_3$ is hydrogen or —$COOR_4$, with the proviso that at least one of $R_2$ and $R_3$ is hydrogen; X is oxa, —COO—, or —$CONR_5$— wherein $R_5$ is hydrogen or alkyl of up to 5 carbon atoms and Y is a direct bond or the radical —$R_6$—$Z_1$—CO—NH—$R_7$—NH—CO—$Z_2$—, wherein $R_6$ is linked to X and represents branched or linear alkylene of up to 7 carbon atoms; $Z_1$ and $Z_2$ are oxa or $NR_5$ and $R_7$ is the diradical of an aliphatic or aromatic diisocyanate, with the proviso that in case Xi is oxa, Y is different from a direct bond, and $R_2$ and $R_3$ are hydrogen; comprising the steps of copolymerizing said monomer (A) and said macromer (B) in the presence of a free radical initiator at the reaction temperature between about 20° to about 150° C., in the presence or absence of a substantially inert diluent, and in the presence of an effective macromer (B) expanding amount of a macromer (B) soluble compound of the formula

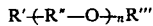

wherein R' is HO—, alkoxy of up to eight carbon atoms or alkanoyloxy of up to eight carbon atoms; R" is straight or branched chain alkylene of two to six carbon atoms; R''' is hydrogen, alkyl of up to eighteen carbon atoms or alkanoyl of up to eighteen carbon atoms; and n is an integer from 1 to about 100, with the proviso that if n is 1 or R" is ethylene, R''' is alkyl of two to eighteen carbon atoms or alkanoyl of three to eighteen carbon atoms, or a mixture thereof; to form said hydrogel; and loading said active agent (a) into said hydrogel.

2. A process according to claim 1, wherein said active agent is incorporated into said hydrogel by adding said active agent to the monomer (A) and said macromer (B) prior to, or during, said copolymerizing of (A) and (b).

3. A process according to claim 1, wherein R' is —OH or alkanoyloxy of up to three carbon atoms, R" is alkylene of two to four carbon atoms, n is 1 and R''' is alkyl of three to six carbon atoms.

4. A process according to claim 1, wherein the compound of Formula II is ethylene glycol monobutyl ether.

5. A process according to claim 1, wherein said water-soluble monoolefinic monomer is 2-hydroxyethyl methacrylate.

6. A process according to claim 1, wherein said active agent is incorporated into said hydrogel by diffusion from an organic solvent medium containing said active agent subsequent to said copolymerizing of (A) and (B).

7. A process according to claim 6, wherein said active agent is a pharmaceutically, insecticidally, or herbicidally effective agent.

8. A process according to claim 7, wherein said active agent is a pharmaceutically effective agent.

9. A process according to claim 1, wherein said active agent is a pharmaceutically insecticidally, or herbicidally effective agent.

10. A process according to claim 9, wherein said active agent is a pharmaceutically effective agent.

11. A process according to claim 1, wherein the compound of Formula II is of the formula $$HO\!-\!(R''\!-\!O)_n\!H \qquad (III)$$

where n has an average value between about 9 and about 60 and R" is alkylene of three to four carbon atoms.

12. A process according to claim 11 wherein n has an average value between about 25 and 40 and R" is isopropylene.

13. A process according to claim 11, wherein n has an average value between 9 and 40 and R" is tetramethylene.

14. A process according to claim 1, wherein said macromer is a polytetramethylene oxide glycol with a molecular weight of about 600 to about 4000, encapped with toluene diisocyanate and reacted with two moles, per mole of said glycol, of a hydroxyalkyl acrylate or methacrylate, wherein alkyl has 2 to 4 carbon atoms.

15. A process according to claim 14, wherein said water-soluble monoolefinic monomer is 2-hydroxyethyl methacrylate.

* * * * *